United States Patent [19]
Blickle et al.

[11] Patent Number: 4,835,305
[45] Date of Patent: May 30, 1989

[54] PROCESS FOR THE PREPARATION OF TRIFLUOROACRYLATES

[75] Inventors: Peter Blickle, Kelkheim; Klaus Hintzer, Burgkirchen; Werner Schwertfeger, Langgöns; Dieter Ulmschneider, Königstein/Taunus, all of Fed. Rep. of Germany

[73] Assignee: Hoechst Aktiengelselschaft, Frankfurt, Fed. Rep. of Germany

[21] Appl. No.: 181,327

[22] Filed: Apr. 13, 1988

[30] Foreign Application Priority Data

Apr. 15, 1987 [DE] Fed. Rep. of Germany ....... 3712816

[51] Int. Cl.$^4$ .............................................. C07C 69/62
[52] U.S. Cl. .................................... 560/219; 560/227
[58] Field of Search ................................ 560/219, 227

[56] References Cited

U.S. PATENT DOCUMENTS

| 2,436,144 | 2/1948 | Howk et al. | 560/227 |
| 2,571,687 | 10/1951 | Dickey, Jr. | 560/219 |
| 2,951,051 | 8/1960 | Tier | 560/227 |
| 3,386,977 | 6/1968 | Kleiner | 560/219 |
| 3,395,174 | 7/1968 | Knell et al. | 560/219 |
| 3,444,150 | 5/1969 | Haas et al. | 560/227 |
| 3,525,758 | 8/1970 | Katsushima et al. | 560/227 |
| 3,654,245 | 4/1972 | Kometani et al. | 560/219 |
| 3,990,989 | 11/1979 | Bjornson et al. | 560/227 |
| 4,173,654 | 11/1979 | Scheren | 560/227 |
| 4,346,235 | 8/1982 | Sonoda | 560/227 |

FOREIGN PATENT DOCUMENTS 3635750 4/1987 Fed. Rep. of Germany .

Primary Examiner—Paul J. Killos

[57] ABSTRACT

A trifluoroacrylate has been prepared by reacting hexafluoropropene with halogen fluorosulfate (halogen X:Cl, Br or I), eliminating the fluorosulfate $CF_3$—CFX—$CF_2$—$OSO_2F$ to give the acid fluoride $CF_3$—CFX—COF, esterifying the acid fluoride and dehalogenating the product using a metal component.

13 Claims, No Drawings

PROCESS FOR THE PREPARATION OF TRIFLUOROACRYLATES

The invention relates to the preparation of trifluoroacrylates by a multistage process using hexafluoropropene as the starting material.

Esters of trifluoroacrylic acid ($CF_2=CF-COOH$) can be employed in the preparation of copolymers which contain -COOR side groups. These copolymers can be used, for example, as ion exchanger resins or membranes after conversion of the ester groups into the free acid or into the salt form.

The preparation of such trifluoroacrylates has already been described a number of times, but the procedures are inconvenient, the starting materials expensive and the yields unsatisfactory.

A further publication (EP-A No. 0,157,039) describes a fourstep process which is improved compared to the above, proceeding from perfluoroallyl fluorosulfate and leading to the desired trifluoroacrylates via adduction of bromine, desulfonation, esterification and elimination of bromine using zinc. However, due to the preparation, the starting material always contains a byproduct whose removal requires considerable effort. For this reason, no yield determination for the first steps is given in the publication. All further process steps in which halogen is adducted or eliminated specify bromine as the halogen. The elimination of fluorine halide to produce a double bond is not described. It was therefore desired to achieve a further improvement and simplification to the process.

The invention relates to a simplified, multistage process for the preparation of trifluoroacrylates of the formula $CF_2=CF-COOR$ (I) in which R represents a branched or unbranched, unsubstituted or halogen-substituted alkyl group having 1 to 6 carbon atoms, in which process (a) hexafluoropropene is reacted with a halogen fluorosulfate of the formula $X-O-SO_2-F$ in which X is chlorine, bromine or iodine, to give $CF_3-CFX-CF_2-OSO_2F$ (II), (b) the acid fluoride $CF_3-CFX-COF$ is preepared from (II) by elimination of $SO_2F_2$, (c) the compound (III) is esterified using a straight-chain or branched, unsubstituted or halogen-substituted, aliphatic alcohol ROH having 1 to 6, preferably 1 to 4, carbon atoms in the alkyl radical R or using an alcohol of this type in which at least one hydrogen atom in the alkyl chain, with the exception of the hydrogen atom in the α-position, is replaced by halogen, to give $CF_3-CFX-COOR$ (IV), and (d) the ester (IV) obtained in dehalogenated using a metal in an aprotic, polar solvent with formation of a double bond to give compounds of the formula (I).

Some of the individual process steps are known from the literature, but their combination has not been described hitherto. It is novel and unexpected that the temperatures which are used in step d) for elimination of mixed halogen, i.e. halogen and fluorine, where halogen denotes chlorine, bromine or iodine, and where the fluorine atom is eliminated from the terminal $CF_3$ group, are 60° to 150° C., preferably 80° to 140° C. Although the elimination of mixed halogen, as defined above, from halogen-fluorine ether esters at temperatures of 100° to 300° C. is known, the halogen here, however, is eliminated from a terminal $HalCF_2$ group (DE-A-2,934,194). In the only example in which a single step process is described for the preparation of the fluorine-organometallic compound and the thermal decomposition thereof in a solvent, the reaction temperature is given at 160° C.

In the process according to the invention, it is also advantageous that separate or complex purification of intermediates is not necessary in any of the process steps. Any byproducts which may be present do not interfere or can easily be removed.

The halogen fluorosulfate $X-OSO_2F$ required to carry out the process according to the invention is prepared, for example, by electrolyzing fluorosulfonic acid in the presence of a conductive salt and reacting the $FSO_2-O-O-SO_2F$ in $FSO_3H$ solution produces with an equimolar amount of chlorine, bromine or iodine. The reaction of $FSO_2-O-O-SO_2F$ with the pertinent halogen can also take place after isolation of the peroxide.

In step (a) in the process according to the invention, halogen fluorosulfate is firstly reacted with hexafluoropropene, and the addition product of the general formula II $CF_3-CFX-CF_2-OSO_2F$ (II), which usually contains a small amount of the bisfluorosulfate $CF_3-CF(OSO_2F)-CF_2-OSO_2F$, is isolated. This impurity is not crucial since it can easily be removed as such or in the form of secondary products in the subsequent reactions.

In process step (b), the fluorosulfate (II) is converted into the acid fluoride $CF_3-CFX-COF$ (III), nucleophilic compounds, such as fluorides in the form of soluble alkali metal fluorides and/or alkaline earth metal fluorides, for example of sodium, potassium, ammonium, rubidium, cesium or magnesium, or trialkylamine having 1 to 6, preferably 1 to 4, carbon atoms in the alkyl radicals, such as triethylamine and tributylamine, alone or in mixtures, serving as catalysts. In the subsequent esterification (c), at least one aliphatic, straight-chain or branched alcohol ROH having 1 to 6, preferably 1 to 4, carbon atoms or, alcohols of this type in which at least one hydrogen atom in the alkyl chain, with the exception of the hydrogen atoms in the α-position, is replaced by halogen, preferably fluorine, is employed, it being possible for the hydrogen fluoride produces to be bound, for example, to a trialkylamine. Examples of the alcohols used are methanol, ethanol, the various propanols and butanols, furthermore 2,2,2-trifluoroethanol, 2,2,3,3-tetrafluoropropanol, 2,2-3,3,4,4,5,5-octafluoropentanol and 1,1,1,3,3,3-hexafluoropropan-2-ol.

According to a preferred embodiment of the process, steps (b) and (c) can be carried out together, i.e. the compound (II) is reacted with one of the alcohols specified in the presence of the abovementioned catalysts.

The dehalogenation of the esters of the general formula (IV) to give the trifluoroacrylates of the general formula $CF_2=CF-COOR$ (I) is generally carried out using a metal such as Mg, Cu or Sn, but preferably with the aid of zinc, in an aprotic polar solvent, such as polyethylene glycol dimethyl ether or nitriles, preferably the dimethyl ether or tetramethyl ether or diethylene glycol (diglyme or tetraglyme) and also benzonitrile. The zinc can be employed as activated zinc or as commercially available zinc dust. This zinc dust can be activated by ultrasound, high-speed stirrers or alternatively chemically by methods known to those skilled in the art.

The invention also relates to fluoroalkyl tetrafluoropropionates of the general formula $CF_3-CFX-COO-CHRR'$ in which X denotes Cl, Br, or I, and R and R', independently of one another, denote hydrogen or perfluoroalkyl or polyfluoroalkyl having 1-4 carbon atoms in the alkyl radical, but R and R' are not simultaneously hydrogen, and also 1,1,1,3,3,3-hexafluoroisopropyl trifluoroacrylate, $CF_2=CF-COO-CH(CF_3)_2$.

In the examples below, P denotes parts by weight and % denotes percentages by weight.

EXAMPLES (1) Formation of $CF_3-CFI-CF_2-OSO_2F$

495 P of peroxydisulfuryl difluoride were added dropwise with cooling to a solution of 634 P of iodine in 1 l of fluorosulfuric acid. The dark green solution was stirred at 25° C. for a further 5 hours so that it no longer had a solid sediment. Hexafluoropropene (HFP) gas was passed into this solution through a glass frit with vigorous stirring. The temperature of the solution was kept at about 35° C. by cooling and by passing in HFP at a suitable rate. When the mixture had become considerably paler, the introduction of HFP was terminated (755 P of HFP consumed) and the mixture was stirred for a further hour. The product was distilled off under reduced pressure, washed with water and dried over $Na_2SO_4$. Yield 1691 P (90% of theory, relative to $IOSO_2F$) B.p. 60° C./135 mbar.

(2) Formation of $CF_3-CFBr-CF_2-OSO_2F$

470 P of bromine were added dropwise to 2 l of a 1.47 molar solution of peroxydisulfuryl difluoride in fluorosulfuric acid. Hexafluoropropene (HFP) was passed into this solution through a glass frit with vigorous stirring. During this procedure, the temperature was kept at about 40° C. by cooling and by passing in HFP at a suitable rate. Towards the end of the reaction, the mixture became considerably paler but continued to take up HFP until the end of the reaction was indicated by the absence of heat evolution (HFP consumption 920 P). The mixture formed two phases of which the lower (1750 P) was separated off as the product phase. The upper phase was transferred dropwise onto ice, after which it was possible to separate off a further organic phase (230 P). After distillation, the combined organic phases gave 1605 P of product (83% of theory relative to $BrOSO_2F$); b.p. 93° C.

(3) 2-Iodotetrafluoropropionyl fluoride $CF_3-CFI-COF$ 10 P of potassium fluoride and 75 P of diglyme were introduced into a glass flask equipped with magnetic stirrer, thermometer, dropping funnel, reflux condenser and downstream cold trap (−78° C.) The batch was heated to about 50° C., and 1128 P of $CF_3-CFI-OSO_2F$ was added dropwise at a rate such that continuous evolution of gas occurrd. When the reaction was complete, the cold trap was warmed to room temperature and the residue was distilled together with the contents of the reaction vessel. Yield 743 P (90.4%) of $CF_3-CFI-COF$. B.p. 61°-62° C.

(4) 2-Bromotetrafluoropropionyl fluoride 20 P of potassium fluoride and 100 P of tetraglyme were reacted with 3026 P of $CF_3-CFBr-CF_2-OSO_2F$ by the procedure of Example 3. Distillation gave 1810 P (86.7%) of $CF_3-CFBr-COF$. B.p. 29°-30° C.

(5) Methyl 2-iodotetrafluoropropionate 64 P of methanol were introduced into a glass flask equipped with magnetic stirrer, thermometer, dropping funnel and reflux condenser, and 220 P of $CF_3-CFI-COF$ were added dropwise while cooling in ice. The batch was stirred for a further 30 minutes at room temperature and poured into water, and the organic phase was washed twice with water and purified by distillation after drying over $Na_2SO_4$. Yield: 202 P (88%) of $CF_3-CFI-COOCH_3$, b.p. 60°-62° C./67 mbar.

(6) Methyl 2-bromotetrafluoropropionate 250 P of methanol were reacted with 599 P of $CF_3-CFBr-COF$ by the procedure of Example 5. Yield 540 P (85.6%) of $CF_3-CFBr-COOCH_3$, b.p. 109°-110° C.

(7) Methyl 2-bromotetrafluoropropionate from $CF_3-CFBr-CF_2-OSO_2F$ 41 P of potassium fluoride and 250 P of methanol were introduced into the apparatus of Example 5. 228 P of a mixture comprising 204 P of $CF_3-CFBr-CF_2-OSO_2F$ and 24 P of $CF_3-CFOSO_2F-CF_2OSO_2F$ were then added dropwide, and exothermic reaction occurring and gas being evolved. After stirring at room temperature overnight, the batch was poured into 600 P of water, and the lower phase was separated off, washed twice with water and dried over sodium sulfate. Distillation gave 114.5 P (77%) of $CF_3-CFBr-COOCH_3$.

(8) Hexafluoroisopropyl iodotetrafluoropropionate 178 P of $CF_3-CFI-COF$ were introduced into a 1,000 ml stirred flask. 104 P of hexafluoroisopropanol were added dropwise over the course of 25 minutes at 19° C. The mixture was cooled to 0° C., and 48.1 P of tributylamine were added over the course of one hour at this temperature (cooling). After a further hour, the reaction mixture was warmed to room temperature, and the crude ester was distilled off at 100 mbar. Subsequent precision distillation over a 30 cm Vigreux column at 100 mbar gave 144 P (52.5%) of $CF_3-CFI-COOCH(CF_3)_2$, b.p. 62°-63° C./100 mbar.

9) Hexafluoroisopropyl 2-bromoetetrafluoropropionate 227 P of $CF_3CFBr-COF$ were introduced into the apparatus of Example 5. A mixture of hexafluoroisopropanol and 74 P of tributylamine was subsequently added dropwise. The internal temperature of the mixture was kept below 22° C. over the entire reaction by cooling in ice. The mixture was subsequently distilled at 65-70 mbar. The crude distillate and the trap contents were redistilled, 296 P (83%) of $CF_3-CFBr-COOCH(CF_3)_2$ being obtained, b.p. 99°-101° C.

(10) Methyl trifluoroacrylate (a) From methyl 2-iodotetrafluoropropionate 23 P of zinc dust, 5 P of $CF_2BR-CFClBr$ and 130 P of benzonitrile were introduced into a glass flask equipped with magnetic stirrer, thermometer, dropping funnel, Vigreux column, column head and downstream cold trap (−78° C). The mixture was heated and gas evolution ($CF_2=CFCl$) commenced at about 110° C. After this activation of the zinc, 71.5 P of $CF_3-CFI-COOCH_3$ were added dropwise at 110° C. and reacted with an exothermic reaction. When the reaction had subsided, the volatile components were stripped off in vacuo (<250 mbar), the bottom temperature being increased to about 150° C. The distillate and trap contents were subsequently fractionated, 28 P of a colorless liquid being isolated, b.p. 84°-88° C., which, according to a gas-chromatographic investigation, comprised more than 96% of $CF_2=CF-COOCH_3$ (Yield about 80%). It was possible to detect $CF_3-CHF-COOCH_3$ as an impurity.

(b) From methyl 2-bromotetrafluoropropionate 39 P of zinc dust, 5 P of $CF_2Br-CFClBr$ and 100 P of $CF_3-CFBr-COOCH_3$ were reacted in 150 P of benzonitrile by the procedure described under (a). Distillation gave 32.5 P (55.5%) of $CF_2=CF-COOCH_3$, b.p. 84°–85° C.

(11) Hexafluoroisopropyl trifluoroacrylate (a) 31.5 P of zinc dust and 130 P of benzonitrile were introduced into a 500 ml stirred flask equipped with distillation bridge. 6.8 P of $CF_2Br-CFClBr$ were initially added dropwise at 135° C., gas evolution and a temperature increase to 145° C. being observed. When the temperature had fallen back to 135° C., 144 P of hexafluoroisopropyl 2-iodoterafluoropropionate were added dropwise over 75 minutes (temp. ~135° C.), some of the trifluoroacrylate formed distilling off. When the dropwise addition was complete, the mixture was allowed to react for a further 30 minutes, and the crude ester was then distilled off at ~200 mbar. The bridge distillate and the crude ester were combined and distilled over a 30 cm Vigreux column. 50.2 P of hexafluoroisopropyl trifluoroacrylate (53.2% of theory), b.p. 88.5°–89° C., were obtained. $CF_3CHF-COOOCH(CF_3)_2$ was detected as an impurity by gas chromatography.

(b) 19.5 of zinc dust and 100 P of benzonitrile were introduced into an apparatus as described in Example 11a, the mixture was heated to 130° C., and 50 mg of iodine were added for activation. 98 P of $CF_3-CFBr-COOCH(CF_3)_2$ were subsequently added dropwise, an exothermic reaction commencing after a short induction period. When the reaction was complete, the product was separated off by distillation and fractionated. Yield 30 P of $CF_2=CF-COOCH(CF_3)_2$, b.p. 88°–89° C., still containing 10 mol-% of $CF_3-CHF-COOCH(CF_3)_2$.

We claim:

1. A process for the preparation of a trifluoroacrylate of the formula $CF_2=CF-COOR$ (I) in which R represents a branched or unbranched, unsubstituted or halogen-substituted alkyl group having 1 to 6 carbon atoms, wherein (a) hexafluoropropene is reacted with a halogen fluorosulfate of the formula $X-O-SO_2-F$ in which X is chlorine, bromine or iodine, to give $CF_3-CFX-CF_2-OSO_2F$ (II), (b) the acid fluoride $CF_3-CFX-COF$ (III) is prepared from (II) by elimination of $SO_2F_2$, (c) the compound (III) is esterified using a straight-chain or branched, unsubstituted or halogen-substituted, aliphatic alcohol ROH having 1 to 6 carbon atoms in the alkyl radical R or using an alcohol of this type in which at least one hydrogen atom in the alkyl chain, with the exception of the hydrogen atom in the α-position, is replaced by halogen, to give $CF_3-CFX-COOR$ (IV), and (d) the ester (IV) obtained is dehalogenated using a metal in an aprotic, polar solvent with formulation of a double bond to give a compound of the formula (I).

2. The process as claimed in claim 1, wherein, in the formula (I), R is an alkyl group having 1 to 4 carbon atoms and halogen denotes fluorine.

3. The process as claimed in claim 1, wherein, in the formula (I), R is a methyl or hexafluoroisopropyl group.

4. The process as claimed in claim 1, wherein in process step b), at least one soluble alkali metal fluoride, alkaline earth metal fluoride or trialkylamine having 1 to 6 carbon atoms in each alkyl radical is employed as catalyst.

5. The process as claimed in claim 4, wherein the alkyl radical of the trialkylamine has 1 to 4 carbon atoms.

6. The process as claimed in claim 1, wherein, in process step (c), at least one aliphatic alcohol having 1–4 carbon atoms, or an alcohol of this type in which the hydrogen atoms, with the exception of the hydrogen atoms in the α-position, are substituted by fluorine is employed.

7. The process as claimed in claim 1, wherein process step (d) is carried out at a temperature of from 60° to 150° C.

8. The process as claimed in claim 7, wherein the temperature is 80° to 140° C.

9. The process as claimed in claim 1, wherein steps (b) and (c) are carried out together.

10. The process as claimed in claim 1, wherein the metal employed is magnesium, copper or tin.

11. The process as claimed in claim 1, wherein the metal employed is zinc.

12. A fluoroalkyl tetrafluoropropionate of the formula $$CF_3 \leq CFX-COO-CHRR'$$

in which X denotes Cl, Br or I and R and R', independently of one another, denote hydrogen or perfluoroalkyl or polyfluoroalkyl having 1–4 carbon atoms in the alkyl radical, but R and R' are not simultaneously hydrogen.

13. 1,1,1,3,3,3-Hexafluoroisopropyl trifluoroacrylate, $CF_2=CF-COO-CH(CF_3)_2$.

* * * * *

UNITED STATES PATENT AND TRADEMARK OFFICE
CERTIFICATE OF CORRECTION

PATENT NO. : 4,835,305

DATED : May 30, 1989

INVENTOR(S) : Peter Blickle, Klaus Hintzer, Werner Schwertfeger and Dieter Ulmschneider It is certified that error appears in the above-identified patent and that said Letters Patent is hereby corrected as shown below:

Column 1, line 43: "preepared" should read --(III) is prepared--.

Column 2, line 14: "produces" should read --produced--.

Column 2, line 44: "duces" should read --duced--.

Column 4, line 15: "dropwide, and" should read --dropwise, an--.

Column 4, line 35: "2-bromoetetrafluoropropion-" should read -- 2-bromotetrafluoropropion- --.

Column 5, line 10 "2-iodoterafluoropropionate" should read --2-iodotetrafluoropropionate--.

UNITED STATES PATENT AND TRADEMARK OFFICE
CERTIFICATE OF CORRECTION

PATENT NO. : 4,835,305

DATED : May 30, 1989

INVENTOR(S) : Peter Blickle, Klaus Hintzer, Werner Schwertfeger and Dieter Ulmschneider It is certified that error appears in the above-identified patent and that said Letters Patent is hereby corrected as shown below:

The formula of claim 12 should read:

$$--CF_3-CFX-COO-CHRR'--.$$

Signed and Sealed this

Twenty-fourth Day of July, 1990

Attest:

HARRY F. MANBECK, JR.

Attesting Officer

Commissioner of Patents and Trademarks